United States Patent
Park et al.

(10) Patent No.: US 11,399,424 B2
(45) Date of Patent: Jul. 26, 2022

(54) POWER SUPPLY APPARATUS FOR X-RAY IMAGING SYSTEM AND MOBILE X-RAY IMAGING SYSTEM HAVING SAME

(71) Applicant: POSKOM CO., LTD., Gyeonggi-do (KR)

(72) Inventors: Jong Rae Park, Seoul (KR); Ki Bong Sung, Gyeonggi-do (KR)

(73) Assignee: POSKOM CO., LTD., Gyeonggi-Do (KR)

( * ) Notice: Subject to any disclaimer, the term of this patent is extended or adjusted under 35 U.S.C. 154(b) by 667 days.

(21) Appl. No.: 16/443,855

(22) Filed: Jun. 17, 2019

(65) Prior Publication Data

US 2020/0008288 A1    Jan. 2, 2020

(30) Foreign Application Priority Data

Jun. 28, 2018   (KR) .......................... 10-2018-0074572

(51) Int. Cl.
*A61B 6/00* (2006.01)
*H05G 1/26* (2006.01)
*H05G 1/54* (2006.01)
*H05G 1/10* (2006.01)
*H01M 10/42* (2006.01)
*H05G 1/12* (2006.01)

(52) U.S. Cl.
CPC .............. *H05G 1/12* (2013.01); *A61B 6/4405* (2013.01); *A61B 6/56* (2013.01)

(58) Field of Classification Search
None
See application file for complete search history.

(56) References Cited

U.S. PATENT DOCUMENTS

2011/0185211 A1* 7/2011 Chiasson .................. G06F 1/30
                                                              714/48

* cited by examiner

*Primary Examiner* — Christopher Braniff
(74) *Attorney, Agent, or Firm* — Ladas & Parry, LLP (57) ABSTRACT

A power supply apparatus for an X-ray imaging system. A capacitor unit including a plurality of capacitor cells is connected in series to a single cell battery, such that the capacitor unit is charged using the single cell battery. Only when respective capacitor cells of the capacitor unit are charged, respective balance circuits corresponding to the respective capacitor cells are controlled to be turned on. When the balancing of the respective capacitor cells is completed, the balance circuits are opened. Accordingly, the power consumption of the capacitor cells is minimized.

7 Claims, 8 Drawing Sheets

POWER SUPPLY APPARATUS FOR X-RAY IMAGING SYSTEM AND MOBILE X-RAY IMAGING SYSTEM HAVING SAME

CROSS REFERENCE TO RELATED APPLICATION

The present application claims priority to Korean Patent Application Number 10-2018-0074572 filed on Jun. 28, 2018, the entire contents of which are incorporated herein for all purposes by this reference.

BACKGROUND

Field

The present disclosure relates to a power supply apparatus and, more particularly, to a power supply apparatus for an X-ray imaging system. In the power supply apparatus, a capacitor unit including a plurality of capacitor cells is connected in series to a single cell battery so that the capacitor unit is charged using the single cell battery. In addition, respective balance circuits corresponding to the respective capacitor cells are controlled to be turned on only when respective capacitor cells of the capacitor unit are charged, and the balance circuits are opened, thereby minimizing the power consumption of the capacitor cells when the balancing of the respective capacitor cells is completed.

Description

An X-ray imaging system is a system that transmits X-rays, generated by a thermal electron collision between a cathode and an anode, through a patient or an animal's body and develops X-ray images of the patient or the animal on a digital image panel or the like to diagnose the physical condition of the patient or animal. The X-ray imaging system is widely used as a system for easily diagnosing a fracture state or an abnormality of an internal organ of a patient or an animal without causing pain to the patient or the animal. In recent years, various X-ray imaging systems have been developed to produce X-ray images of patients and animals with ease and accuracy. Particularly, a mobile X-ray imaging system is fabricated to be movable in order to easily and directly produce an X-ray image of a patient or an animal and immediately diagnose the physical state of the patient or the animal in an intended place.

Figure 1:
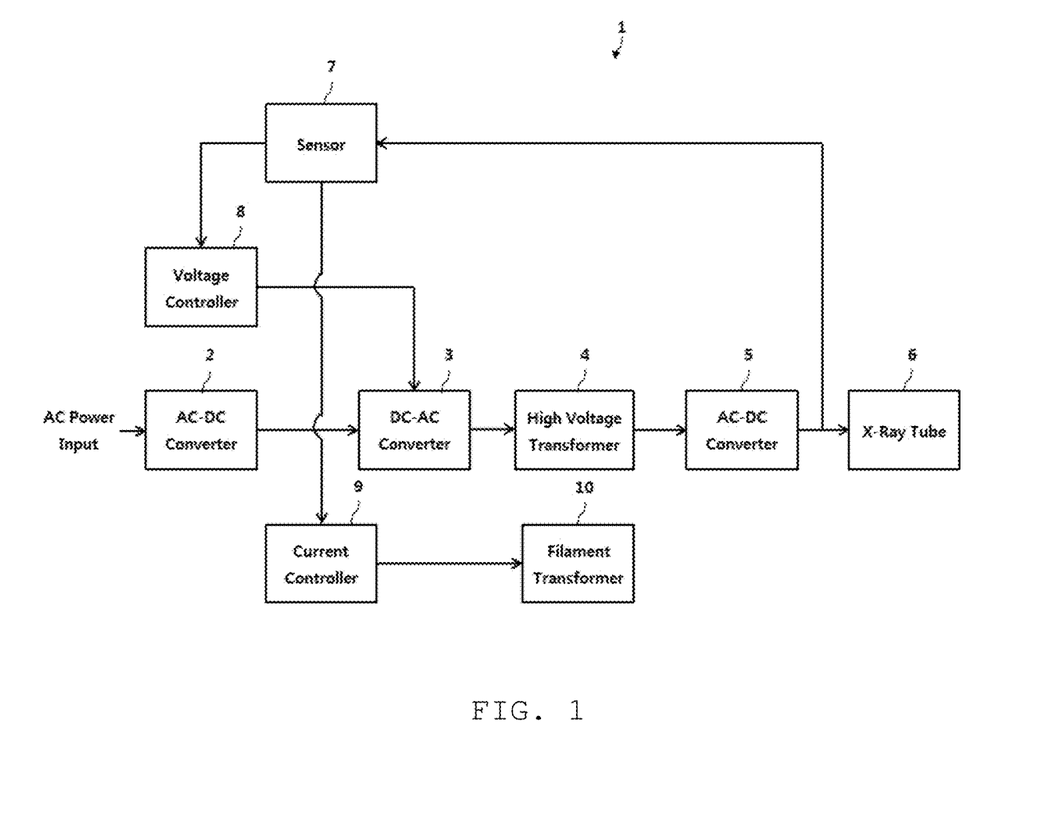
FIG. 1 is a block diagram illustrating a conventional mobile X-ray imaging system using a commercial power source.

FIG. 1 is a functional block diagram illustrating a conventional mobile X-ray imaging system using a commercial power source.

Referring to FIG. 1, the conventional mobile X-ray imaging system 1 includes an AC-DC converter 2 for converting input commercial AC power into DC power, a DC-AC converter 3 for converting DC power converted by high-speed switching into high-frequency AC power of 20 KHz to 300 KHz, a high-voltage transformer 4 for boosting the converted AC power to high-voltage AC power, and an AC-DC converter 5 for converting the boosted high-voltage AC power to high-voltage DC power and applying the high-voltage DC power to an X-ray tube 6. The X-ray tube 6 has a cathode filament disposed in a vacuum glass tube and an anode separated opposite to the cathode filament. When a current is applied to the cathode filament, heated electrons are generated in the cathode filament. The heated electrons are accelerated and collide with the anode due to the potential difference applied from the AC-DC converter 5 so that X-rays are generated in this process.

A sensor 7 detects the magnitude of a voltage applied to the X-ray tube 6 and the magnitude of a current flowing through the filament of the X-ray tube 6 and supplies the detected voltage and current to a voltage controller 8 and a current controller 9, respectively. Based on the magnitude of the detected voltage, the voltage controller 8 generates a pulse signal to control the voltage magnitude, and adjusts a switching-on/off period of the DC-AC converter 3 based on the generated pulse signal to control the frequency of the AC power generated through the conversion from the DC power in the DC-AC converter 3. In addition, the current controller 9 controls the magnitude of the current output from the filament transformer 10 based on the magnitude of the current detected by the sensor 7 to ultimately control the magnitude of the current flowing through the X-ray tube 6.

Figure 2:
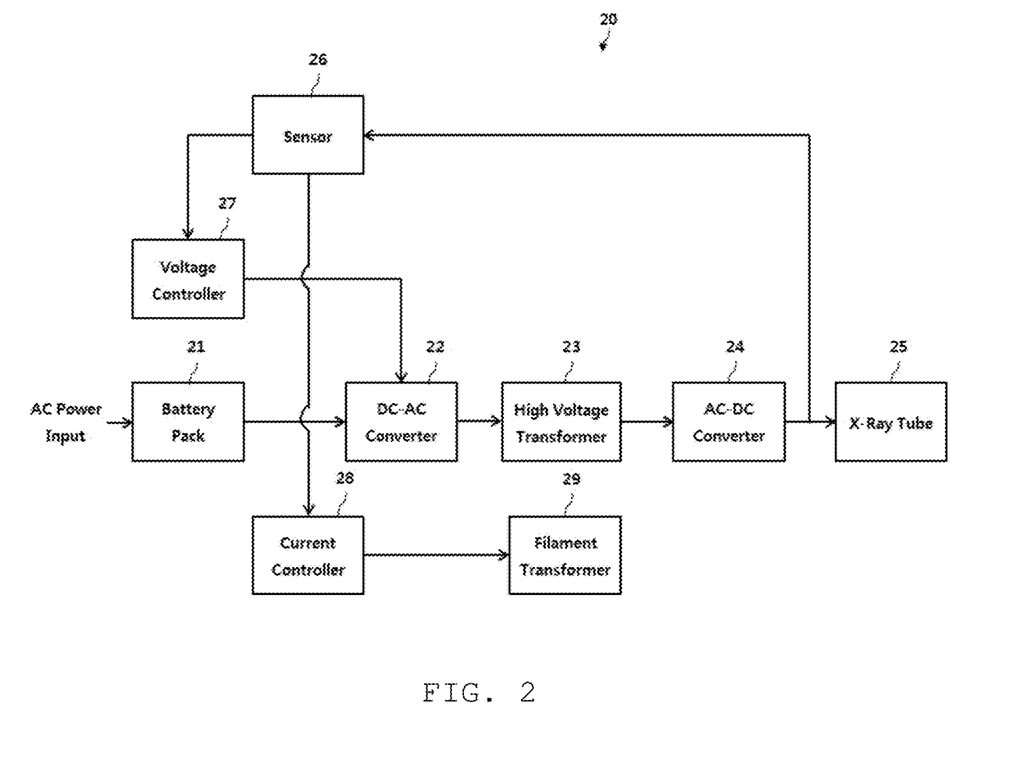
FIG. 2 is a block diagram illustrating a conventional mobile X-ray imaging system using a battery as a power supply.

FIG. 2 is a functional block diagram illustrating a conventional mobile X-ray imaging system 20 using a battery as a power supply.

Referring to FIG. 2, the conventional mobile X-ray imaging system includes a battery pack 21 in which a plurality of batteries are connected in series, a DC-AC converter 22 for converting DC power applied from the battery pack 21 by high-speed switching into high-frequency AC power of 20 KHz to 300 KHz, a high-voltage transformer 23 for boosting the converted AC power to high-voltage AC power, an AC-DC converter 24 for converting the boosted high-voltage AC power to high-voltage DC power, and an X-ray tube 25 generating X-rays using the high-voltage DC power applied from the AC-DC converter 24.

A sensor 26, a voltage controller 27, a current controller 28, and a filament transformer 29 operate in the same manner as the sensor 7, the voltage controller 8, the current controller 9, and the filament transformer 10, illustrated in FIG. 1, so as to control the magnitude of a DC voltage applied to the X-ray tube 25 and a current applied to the filament.

Since the conventional mobile X-ray imaging system 1 using the commercial power source as illustrated in FIG. 1 uses a commercial power source as an operating power supply of the X-ray imaging system 1, the conventional mobile X-ray imaging system has inconvenience in use in that the imaging system can be used only in a place where a commercial power source is available, or commercial power is required to be drawn to the place where the X-ray imaging system 1 is used through a long power cable.

As illustrated in FIG. 2, the conventional mobile X-ray imaging system 20 using the battery pack has a problem in that the plurality of batteries are required to be connected in series since high-voltage DC power is only generated using the battery pack.

Therefore, the conventional mobile X-ray imaging system using the battery pack has a large volume and weight, which is inconvenient to use when a user uses the mobile X-ray imaging system 20 while simply moving the X-ray imaging system.

Figure 3:
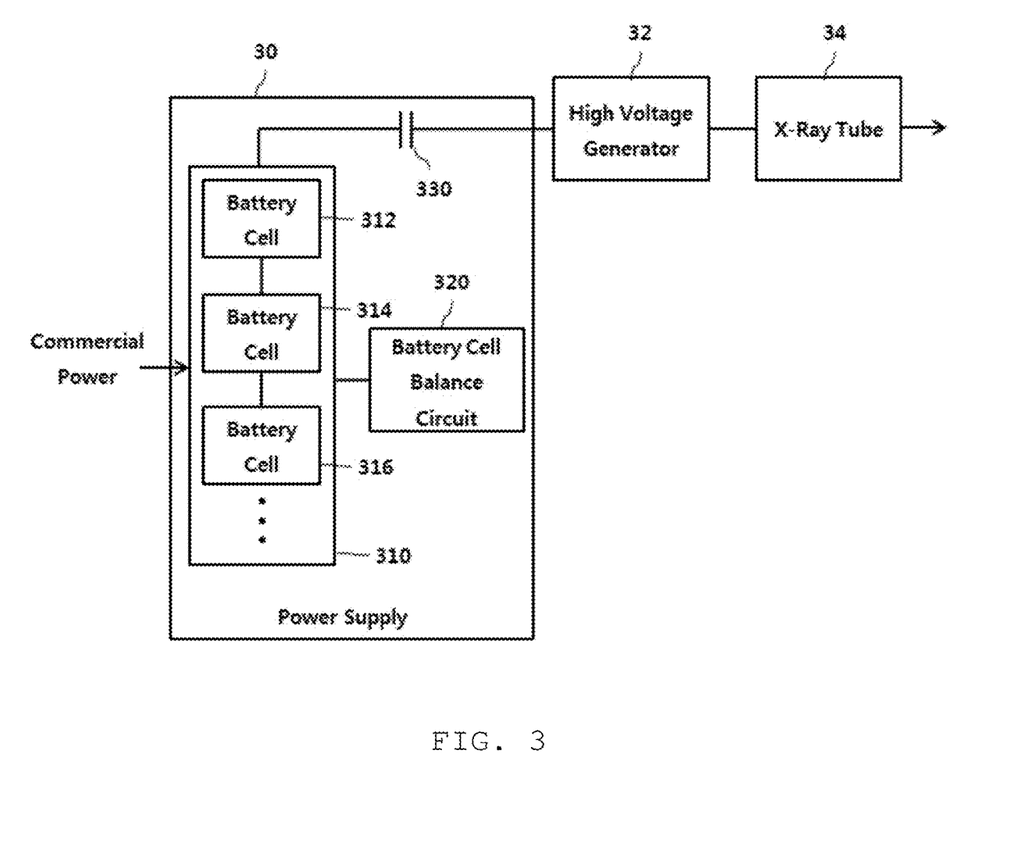
FIG. 3 is a circuit diagram illustrating a conventional mobile X-ray imaging system in which a battery pack including a plurality of battery cells and one or more capacitors are connected in series, and a balance circuit for the balancing between battery cells is provided.

FIG. 3 is a circuit diagram illustrating a conventional mobile X-ray imaging system in which a battery pack 310 including a plurality of battery cells 312, 314 and 316 and one or more capacitors 330 are connected in series, so that the capacitors 330 are charged using the battery pack 310 in order to supply power to the X-ray imaging system.

A high voltage is generated by a high-voltage generator 32 using the power supplied by a power supply 30, and an X-ray tube 34 generates X-rays using the high voltage. As illustrated in FIG. 3, the battery pack 310 includes the plurality of battery cells 312, 314, and 316, so that a battery cell balancing circuit 320 for balancing battery cells is required. Further, because the battery pack includes the plurality of battery cells, even if only one battery cell fails, the whole battery pack fails to operate, so as to reduce the battery life. In addition, since the battery pack is heavy, it is inconvenient to carry. Further, since the battery pack is charged using a commercial power source, it is difficult to easily charge the battery pack with a low voltage automobile charger or a universal serial bus (USB) charger.

Further, in the case of the conventional mobile X-ray imaging system illustrated in FIG. 3, when a plurality of capacitors is used, a capacitor balance circuit for balancing the plurality of capacitors is additionally required. Due to the power consumption by the capacitor balance circuit, electric power charged once in the capacitors is automatically consumed over time even if the mobile X-ray imaging system is not used. This causes a problem of reducing the use time of the battery pack.

The information disclosed in the Background section is only provided for a better understanding of the background and should not be taken as an acknowledgment or any form of suggestion that this information forms prior art that would already be known to a person skilled in the art.

BRIEF SUMMARY

The present disclosure has been made in consideration of the above-described problems occurring in the related art. Various aspects of the present disclosure provide a power supply apparatus for an X-ray imaging system, which has a light and compact structure with improved mobility by using low battery power of a single battery cell as operating power, such that a circuit for adjusting the balance between battery cells is omitted.

Also provided is a power supply apparatus for an X-ray imaging system, in which a charging voltage of a capacitor unit is detected, and when the balancing of the capacitor unit is determined to be completed, capacitor balance circuits corresponding to respective capacitor cells are controlled to be turned off, so that electric power charged in the respective capacitor cells is not consumed by the capacitor balance circuits. Accordingly, a standby time can be extended, and even after a long standby time, rated power required for generation of X-rays can be quickly supplied, due to a very small amount of electric power having been discharged from the capacitor unit.

Also provided is a power supply apparatus for an X-ray imaging system, in which a battery pack can be charged using not only a commercial power source but also a low voltage supplied by an automobile charger, a solar cell, or the like.

Also provided is an X-ray imaging system having a light and compact structure with improved mobility, in which low battery power of a single battery cell is used as operating power, such that a circuit for adjusting a balance between battery cells is omitted.

Exemplary embodiments may provide a power supply apparatus for an X-ray imaging system, the power supply apparatus including: a battery pack having a single cell so that the battery pack is charged with power and outputs the charged power using the single cell; a capacitor unit connected in series with the battery pack and including a plurality of capacitor cells charged with power; a capacitor balance unit including a plurality of balance circuits corresponding to respective capacitor cells of the capacitor unit to balance the capacitor cells so that when the balance circuit corresponding to the capacitor cell overcharged during charging of the capacitor unit is turned on, energy of the overcharged capacitor cell is consumed; a sensor detecting a voltage of each capacitor cell of the capacitor unit during charging of the capacitor unit; and a charge controller configured to, when overcharge or non-charging of the capacitor cell is detected through the sensor, control the overcharged or non-charged capacitor cell to be turned on or off so as to control the balancing of the overcharged capacitor cell.

The charge controller may charge the capacitor unit together when the battery pack is charged. Further, the charge controller may open the balance circuit when the charging of the capacitor unit is completed to cut off a current consumed by the balance circuit so as to minimize the discharge of the capacitor cell.

The balance circuit may include a resistor consuming energy of the overcharged capacitor cell and a switch turning on or off a connection with the resistor so that the energy of the overcharged capacitor cell is consumed. The battery pack may be charged by any one of a universal serial bus (USB) charger, a wireless charger, a mobile phone auxiliary battery, and a commercial power source.

Exemplary embodiments may provide an X-ray imaging system including: a power supply apparatus; a high-voltage generator generating high-voltage DC power using the power from the power supply apparatus; and an X-ray generator generating X-rays using the generated high-voltage DC power, the power supply apparatus including: a battery pack having a single cell so that the battery pack is charged with power and outputs the charged power using the single cell; a capacitor unit connected in series with the battery pack and including a plurality of capacitor cells charged with power; a capacitor balance unit including a plurality of balance circuits, each having a switch and a resistor, and corresponding to respective capacitor cells of the capacitor unit to balance the capacitor cells so that when the switch is turned on for the capacitor cell overcharged during charging of the capacitor unit, energy of the overcharged capacitor cell is consumed through the resistor; a sensor detecting a voltage of each capacitor cell of the capacitor unit during charging of the capacitor unit; and a charge controller, wherein, when overcharge of the capacitor cell is detected through the sensor, the charge controller controls the switch of the corresponding balance circuit to be turned on or off so as to control the balancing of the overcharged capacitor cell.

The high-voltage generator may receive the DC power of the battery pack and the capacitor unit connected in series to generate the high-voltage DC power.

According exemplary embodiments, in the power supply apparatus for an X-ray imaging system and the mobile X-ray imaging system, only a single cell is used in the battery pack, and low-capacity battery power is used, such that compact X-ray imaging system can be fabricated to be remarkably lightweight, so that a user can easily carry the X-ray imaging system.

In the power supply apparatus for an X-ray imaging system, it is possible to generate high operating power of the X-ray imaging system from a low level of battery power by supplying the battery power to the X-ray imaging system by connecting the battery pack including the single cell and the plurality of capacitor power sources in series.

In the power supply apparatus for an X-ray imaging system, a charging voltage of the capacitor unit is detected, and when the balancing of the capacitor unit is determined to be completed, capacitor balance circuits corresponding to respective capacitor cells are controlled to be turned off, so that electric power charged in the respective capacitor cells is not consumed by the capacitor balance circuits. Accordingly, a standby time can be extended, and even after a long standby time, rated power required for generation of X-rays can be quickly supplied, due to a very small amount of electric power having been discharged from the capacitor unit.

In the power supply apparatus for an X-ray imaging system, since a single cell is used for the battery pack, the circuit for adjusting the balance between the battery cells is not required, the lifetime is extended, and a battery protection circuit can be easily realized.

In the power supply apparatus for an X-ray imaging system, since the capacitor unit in which the plurality of capacitors are connected in series is used, when a high operation voltage is required, the power supply apparatus can be easily modified by simply increasing the number of capacitors.

In the power supply apparatus for an X-ray imaging system, since the power supply apparatus uses the battery pack having a low power level, it is possible to charge the battery pack using a low voltage, supplied by an automobile charger, a solar cell, a wireless charger, a mobile phone auxiliary battery, a USB charger, or the like.

BRIEF DESCRIPTION OF THE DRAWINGS

The above and other objects, features and advantages of the present disclosure will be more clearly understood from the following detailed description when taken in conjunction with the accompanying drawings, in which.

DETAILED DESCRIPTION

Hereinafter, exemplary embodiments of the present disclosure will be described in detail with reference to the accompanying drawings. It should be understood that the embodiments and configurations described herein are merely exemplary embodiments of the invention and are not intended to represent all of the technical ideas of the present disclosure, and therefore various equivalents and variations to substitute the exemplary embodiments may be provided.

Figure 4:
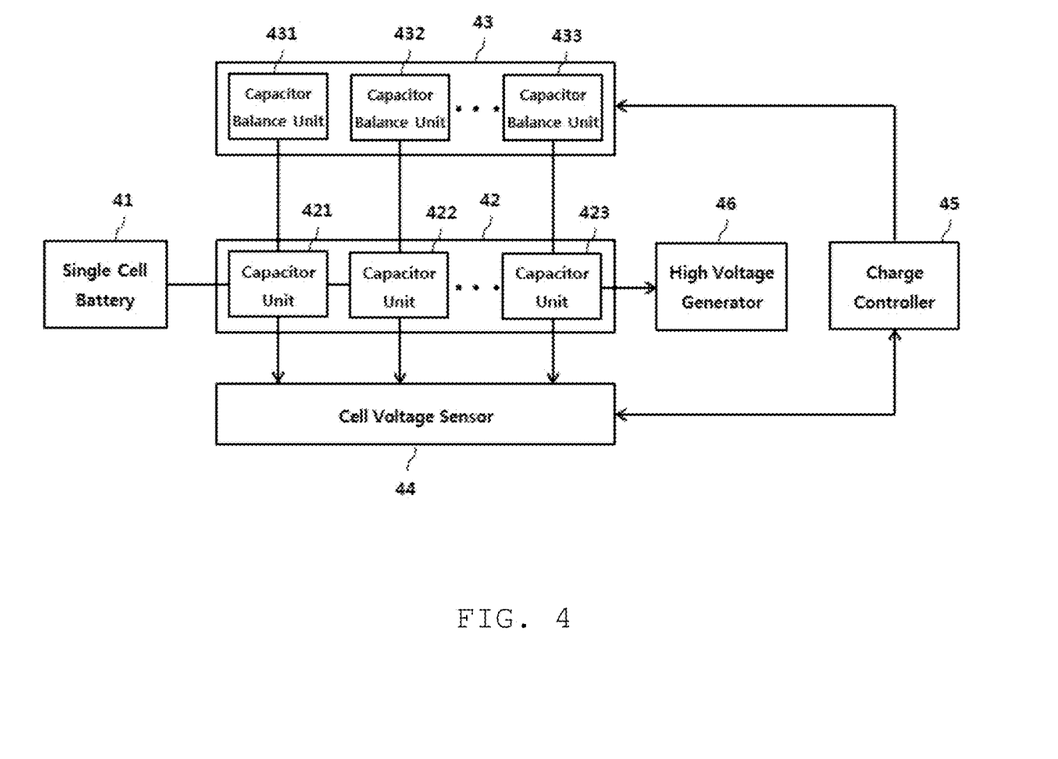
FIG. 4 is a block diagram illustrating a configuration of a power supply apparatus for a mobile X-ray imaging system according to exemplary embodiments.

FIG. 4 is a block diagram illustrating a configuration of a power supply apparatus for a mobile X-ray imaging system according to exemplary embodiments.

The power supply apparatus for an X-ray imaging system includes a single-cell battery 41, a capacitor unit 42, a capacitor balance unit 43, a cell voltage sensor 44, and a charge controller 45.

The single-cell battery 41 has a single cell so that the battery pack is charged with power through the single cell and outputs the charged power. In exemplary embodiments, the power supply apparatus is configured such that the battery pack includes a single cell, whereas the capacitor unit includes a plurality of capacitor cells. The use of the single battery cell allows a user to directly use today's charging infrastructures for mobile phones. For example, the single-cell battery 41 having the single cell may be charged using any one of, but not limited to, a USB charger, a wireless charger, a mobile phone auxiliary battery, and a commercial power source.

In addition, since the battery pack is comprised of a single cell, it is easy to implement a battery protection circuit, and a circuit for adjusting the balance between the battery cells is not required. Further, in the case where the battery pack is comprised of a plurality of battery cells, even if either of the battery cells fails, the entire battery pack fails to operate. However, in the case where the battery pack is comprised of a single battery cell, the battery pack may have extended lifetime. In addition, by using the single cell battery pack, the weight of the battery pack may be reduced, so that the X-ray imaging system may be lightened remarkably.

The capacitor unit 42 is connected in series with the single cell battery 41, and includes a plurality of capacitor cells 421, 422 and 423, which are charged with power through the single-cell battery 41. In order to output a large quantity of X-ray energy even with a small capacity battery, the power supply apparatus is configured such that the plurality of capacitor cells are connected in series so that electric power charged in the capacitor cells is used as operating power.

The capacitor balance unit 43 includes a plurality of capacitor balance circuits 431, 432 and 433 corresponding to the plurality of capacitor cells 421, 422 and 423 of the capacitor unit 42, respectively. When the capacitor balance circuit corresponding to the capacitor cell overcharged during charging of the capacitor unit 42 is turned on, the energy of the overcharged capacitor cell is consumed so that the cells of the capacitor unit 42 are balanced.

Each of the plurality of capacitor balance circuits 431, 432 and 433 may include a resistor (not shown) consuming the energy of the overcharged capacitor cell, and a switch (not shown) turning on/off the connection with the resistor for the energy consumption of the overcharged capacitor cell. As the switch, a field effect transistor (FET) may be used.

The cell voltage sensor 44 detects a voltage of each capacitor cell of the capacitor unit 42 during the charging of the capacitor unit 42.

When overcharge or non-charge of the capacitor cell is detected through the cell voltage sensor 44, the charge controller 45 turns on/off the capacitor balance circuit corresponding to the capacitor cell that is overcharged or non-charged, so as to control the balancing of the overcharged capacitor cell.

The charge controller 45 may be configured to charge the single cell battery 41 together with the capacitor unit 42. When the single battery cell and the plurality of capacitor cells are charged together as described above, the energy stored in the battery pack and the energy stored in the capacitor cells can be used together in actual use so as to increase the use time. More specifically, the charge controller 45 first charges the single cell battery 41 and then the capacitor unit 42 when charging the single cell battery 41 and the capacitor unit 42. In addition, the charge controller is configured to start controlling the single cell battery 41 and the capacitor unit 42 to be simultaneously charged when the single cell battery cell 41 has been charged to at least a threshold level set on the basis of the charging capacity of the single cell battery 41.

More particularly, the charge controller 45 may be configured to control respective capacitor balance circuits corresponding to respective capacitor cells 421, 422, and 423 to be turned on only when the respective capacitor cells 421, 422, and 423 of the capacitor unit 42 are charged, so that the balance between the capacitor cells 421, 422, and 423 is maintained, and control the respective capacitor balance circuits 431, 432, and 433 to be turned off when the balance between the capacitor cells 421, 422 and 423 is maintained.

When the balance between the capacitor cells 421, 422 and 423 is maintained, the capacitor balance circuits 431, 432 and 433 are turned off so that electric power charged in the capacitor cells 421, 422, and 423 is not consumed by the capacitor balance circuits and thus the discharge of the capacitor cells are minimized. Therefore, the power supply apparatus for an X-ray imaging system according to exemplary embodiments is able to extend a standby time in a state in which the power is charged in the capacitor unit 42 and quickly supplying a rated power required for generating X-rays due to a very small discharge of the capacitor unit 42 even after an extended standby time.

Figure 5:
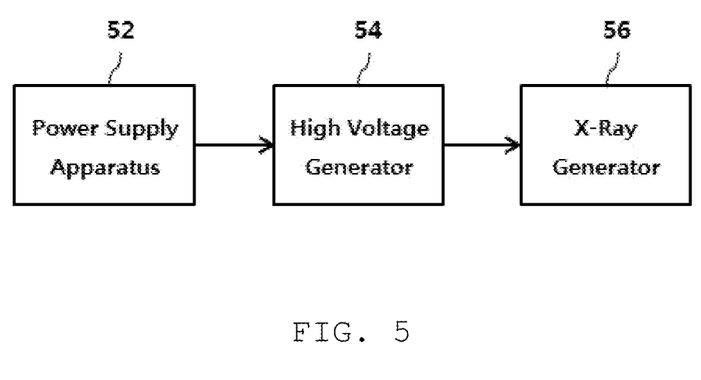
FIG. 5 is a block diagram illustrating a configuration of a mobile X-ray imaging system having the power supply apparatus according to exemplary embodiments.

FIG. 5 is a block diagram illustrating a configuration of a mobile X-ray imaging system having the power supply apparatus according to exemplary embodiments.

In exemplary embodiments, the X-ray imaging system includes a power supply apparatus 52, a high-voltage generator 54, and an X-ray generator 56. The power supply apparatus may be a power supply apparatus for an X-ray imaging system illustrated in FIG. 4. The power supply apparatus includes: a single-cell battery 41 having a single cell to be charged with power using the single cell and output the charged power; a capacitor unit 42 connected in series with the single-cell battery 41 and including a plurality of capacitor cells 421, 422, and 423; a capacitor balance unit including a plurality of balance circuits 431, 432, and 433 corresponding to respective capacitor cells of the capacitor unit 42, respectively, each of the plurality of balance circuits 431, 432, and 433 having a switch and a resistor, wherein, when the switch is turned on for the capacitor cell overcharged during charging of the capacitor unit 42, energy of the overcharged capacitor cell is consumed through the resistor to balance the capacitor cells; a sensor 44 detecting a voltage of each capacitor cell 421, 422, or 423 of the capacitor unit 42 during charging of the capacitor unit 42; and a charge controller 45, wherein, when overcharge of the capacitor cell is detected through the sensor 44, the charge controller controls the switch of the corresponding capacitor balance circuit of the capacitor balance unit 43 to be turned on or off so as to control the balancing of the overcharged capacitor cell.

The high-voltage generator 54 generates high-voltage DC power using the power from the power supply apparatus 52. The high-voltage generator 54 may receive the DC power of the single-cell battery 41 and the capacitor unit 42 connected in series to generate the high-voltage DC power.

The X-ray generator 56 generates X-rays using the high-voltage DC power.

Figure 6:
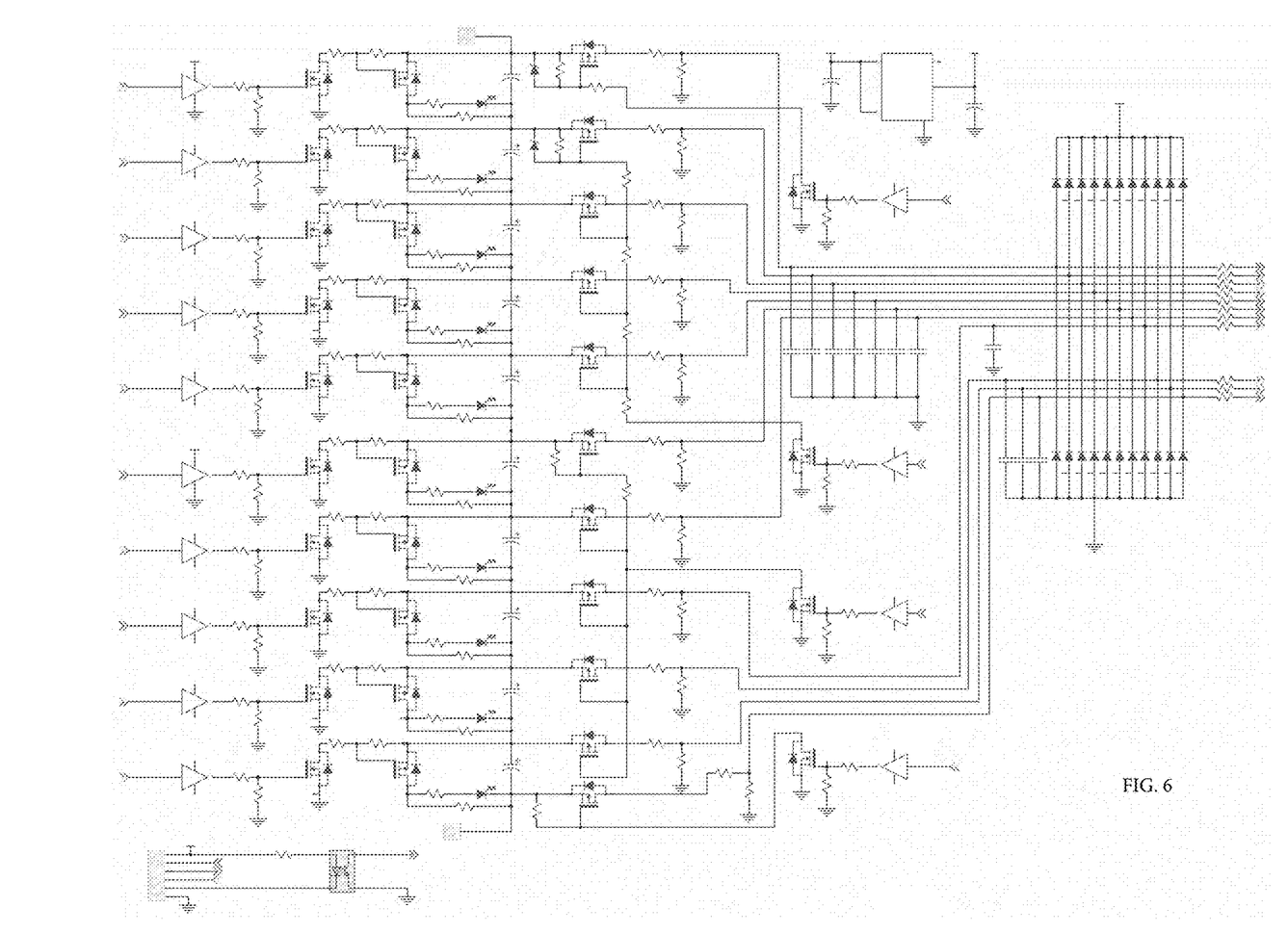
FIG. 6 is a circuit diagram illustrating a capacitor balance circuit of a power supply apparatus for a mobile X-ray imaging system according to exemplary embodiments.
Figure 7:
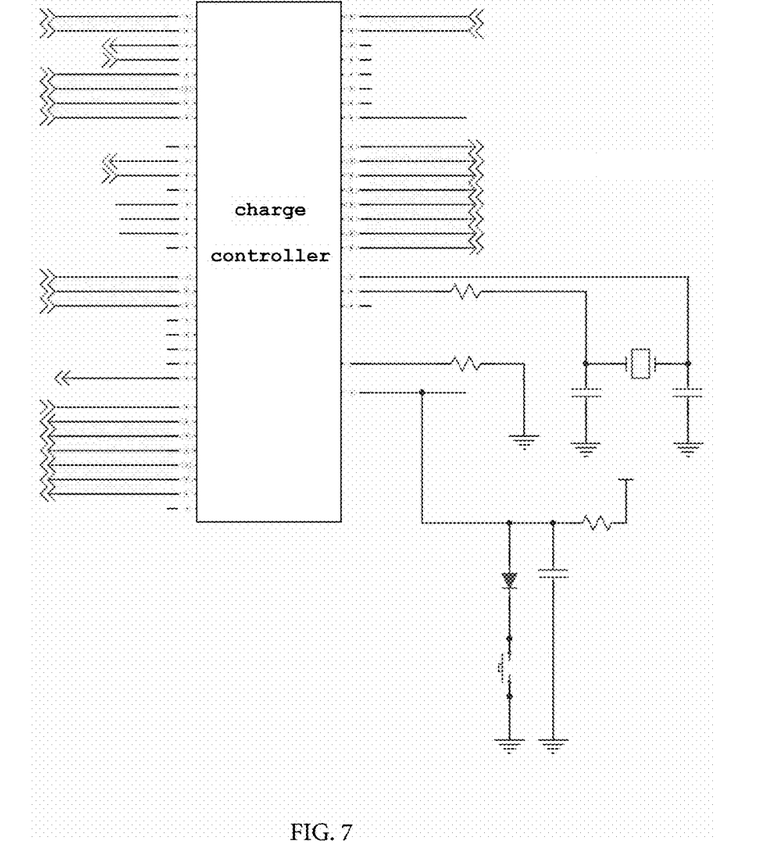
FIG. 7 is a circuit diagram illustrating a charge controller of a power supply apparatus for a mobile X-ray imaging system according to exemplary embodiments.
Figure 8:
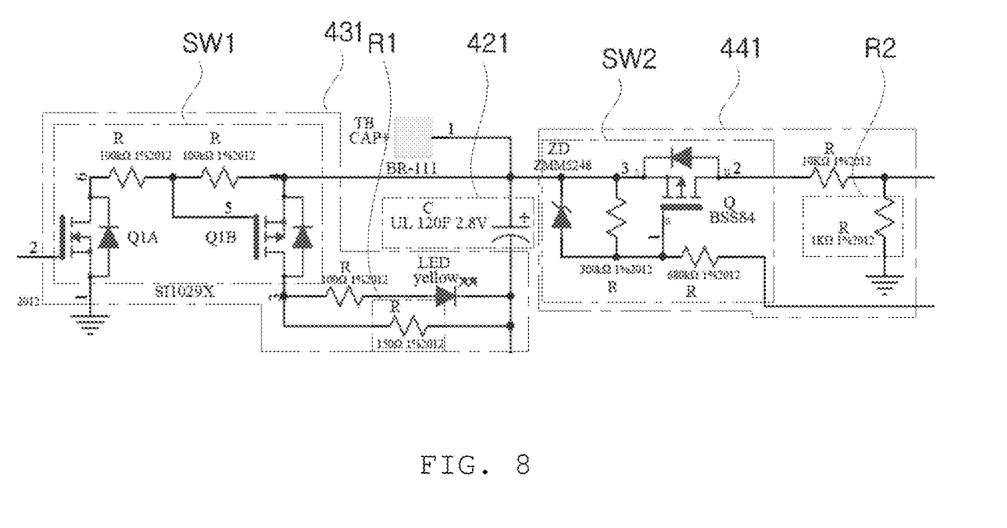
FIG. 8 is a circuit diagram showing an enlarged view of the unit circuit of FIG. 6

FIG. 6 is a circuit diagram illustrating a capacitor balance circuit of a power supply apparatus for a mobile X-ray imaging system according to exemplary embodiments, and FIG. 7 is a circuit diagram illustrating a charge controller of a power supply apparatus for a mobile X-ray imaging system according to exemplary embodiments. FIG. 8 is a circuit diagram showing an enlarged view of the unit circuit of FIG. 6.

The power supply apparatus for an X-ray imaging system according to the present invention includes a unit circuit for charging power to each capacitor cell. As shown in FIG. 8, a capacitor balance circuit 431 includes a first switch sw1 that operates as an FET and a resistor R1 that consumes energy of the overcharged capacitor cell 421.

The cell voltage sensing unit 441 includes a resistor R2 for detecting the voltage of the capacitor cell 421 and a second switch SW2 for turning on/off the operation of the cell voltage sensing unit.

The charge controller monitors the power charge amount of each capacitor cell 421 by turning on/off the second switch sw2 of each unit circuit and performs balancing between the capacitor cells by turning on/off the first switch sw1. The charge controller turns off the first switch Sw1 and the second switch SW2 when the balancing between all the capacitor cells is completed. Thus, the charge controller prevents the power charged in the capacitor cell from being consumed by the capacitor balancing circuit 431 or the cell voltage sensing unit 441.

While the present disclosure has been described with reference to certain exemplary embodiments illustrated in the drawings, these embodiments are illustrative only. Rather, it will be understood by a person skilled in the art that various modifications and equivalent other embodiments may be made therefrom. Therefore, the true scope of the present disclosure shall be defined by the concept of the appended claims.

What is claimed is:

1. A power supply apparatus for an X-ray imaging system, comprising:
a battery pack having a single cell to be charged with power using the single cell and output the charged power;
a capacitor unit connected in series with the battery pack and comprising a plurality of capacitor cells charged with power;
a capacitor balance unit comprising a plurality of balance circuits corresponding to capacitor cells of the capacitor unit, respectively, wherein, when the balance circuit corresponding to the capacitor cell overcharged during charging of the capacitor unit is turned on, energy of the overcharged capacitor cell is consumed to balance the capacitor cells;
a sensor detecting a voltage of each capacitor cell of the capacitor unit during charging of the capacitor unit; and
a charge controller, wherein, when overcharge or non-charging of the capacitor cell is detected through the sensor, the charge controller controls the overcharged or non-charged capacitor cell to be turned on or off so as to control the balancing of the overcharged capacitor cell.

2. The power supply apparatus according to claim 1, wherein the charge controller charges the capacitor unit together when the battery pack is charged.

3. The power supply apparatus according to claim 2, wherein the charge controller opens the balance circuit when the charging of the capacitor unit is completed to cut off a current consumed by the balance circuit so as to minimize the discharge of the capacitor cell.

4. The power supply apparatus according to claim 1, wherein the balance circuit includes a resistor consuming energy of the overcharged capacitor cell, and a switch turning on or off of a connection with the resistor for energy consumption of the overcharged capacitor cell.

5. The power supply apparatus according to claim 1, wherein the battery pack is charged by one of a universal serial bus charger, a wireless charger, a mobile phone auxiliary battery, and a commercial power source.

6. An X-ray imaging system comprising:
a power supply apparatus;
a high-voltage generator generating high-voltage direct current power using the power from the power supply apparatus; and
an X-ray generator generating X-rays using the generated high-voltage direct current power, the power supply apparatus comprising:
   a battery pack having a single cell to be charged with power using the single cell and output the charged power;
   a capacitor unit connected in series with the battery pack and including a plurality of capacitor cells charged with power;
   a capacitor balance unit including a plurality of balance circuits corresponding to capacitor cells of the capacitor unit, respectively, each of the plurality of balance circuits having a switch and a resistor, wherein, when the switch is turned on for the capacitor cell overcharged during charging of the capacitor unit, energy of the overcharged capacitor cell is consumed through the resistor to balance the capacitor cells;
   a cell voltage sensor detecting a voltage of each capacitor cell of the capacitor unit during charging of the capacitor unit; and
   a charge controller, wherein, when overcharge of the capacitor cell is detected through the cell voltage sensor, the charge controller controls the switch of the corresponding balance circuit to be turned on or off so as to control the balancing of the overcharged capacitor cell.

7. The X-ray imaging system according to claim 6, wherein the charge controller opens the balance circuit when the charging of the capacitor unit is completed to cut off a current consumed by the balance circuit so as to minimize the discharge of the capacitor cell.

\* \* \* \* \*